United States Patent [19]

Tanabe et al.

[11] Patent Number: 5,015,386
[45] Date of Patent: May 14, 1991

[54] METHOD FOR SEPARATION OF ELECTROLYTES, AND METHOD FOR ION EXCHANGE OF ELECTROLYTES WITH COUNTER-IONS

[75] Inventors: Toshiya Tanabe; Shigemitsu Abe; Masazumi Date; Tetsuya Kawakita, all Kawasaki, Japan

[73] Assignee: Ajinomoto Co., Inc., Tokyo, Japan

[21] Appl. No.: 220,597

[22] Filed: Jul. 18, 1988

[30] Foreign Application Priority Data

Jul. 20, 1987 [JP] Japan ................. 62-180852

[51] Int. Cl.⁵ .............................. E01D 61/02
[52] U.S. Cl. ................................... 210/638
[58] Field of Search .................. 210/638, 650–655

[56] References Cited

U.S. PATENT DOCUMENTS 4,659,474 4/1987 Perry et al. ............... 210/638

OTHER PUBLICATIONS

Freeman, Scott D. N. et al., "Comparison of Two Thin-Film Composite Membranes: Low Pressure FT-30 to Very Low Pressure NF40HF", *Desalination* 62 (1987) pp. 183–191.

Chemical Abstracts, vol. 103, No. 12, Sep. 23, 1985, Columbus, Ohio, U.S.A., p. 365, abstract No. 93439h; K. Koyama et al.: "Separation of inorganic ions by charged reverse osmosis membranes"; & Maku 1984, 9(5), 281-4 (Japan).

Journal Water Pollution Control Federation, vol. 51, No. 1, Jan. 1979, pp. 176–186; D. Bhattacharyya et al.: "Charged membrane ultrafiltration of heavy metals from nonferrous metal" p. 179, lines 9–18.

Journal of Chemical Engineering of Japan, vol. 15, No. 5, 1983, Tokyo, pp. 394–399; I. Jitsuhara et al.: "Rejection of inorganic salts by charged ultrafiltration membranes made of sulfonated polyfulfone".

CZ-Chemie-Technik, 2. Jahrgang (1973), No. 6, Heidelberg, pp. 245–253; K. Marquardt: "Umgekehrte Osmose und Ultrafiltration -Anwendungsmoeglichkeiten und Beschraenkungen des Verfahrens sowie der gegenwaertige Trend im Anlagenbau" p. 249, table 1, lines 32–36.

*Primary Examiner*—Ivars Cintins
*Attorney, Agent, or Firm*—Oblon, Spivak, McClelland, Maier & Neustadt

[57] ABSTRACT

A method for separating electrolytes which have different charges of the same sign or of carrying out ion exchange of electrolytes with counterions, which comprises causing the electrolytes (anion or cation) to pass through a positively or negatively charged loose reverse-osmotic membrane, in an aqueous solution.

3 Claims, 4 Drawing Sheets

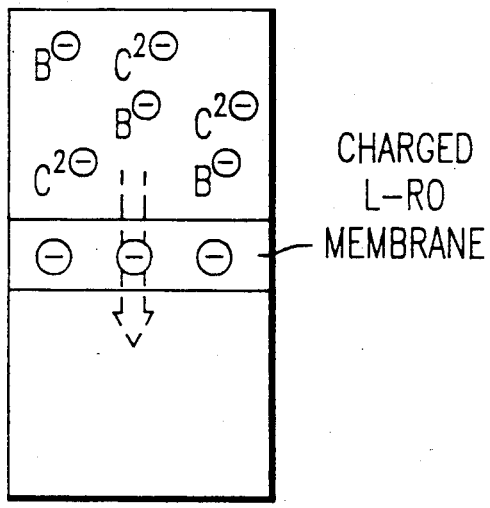 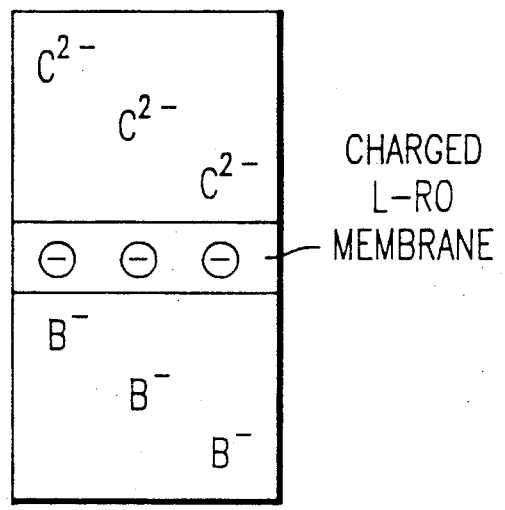
*FIG. 2A*  *FIG. 2B*

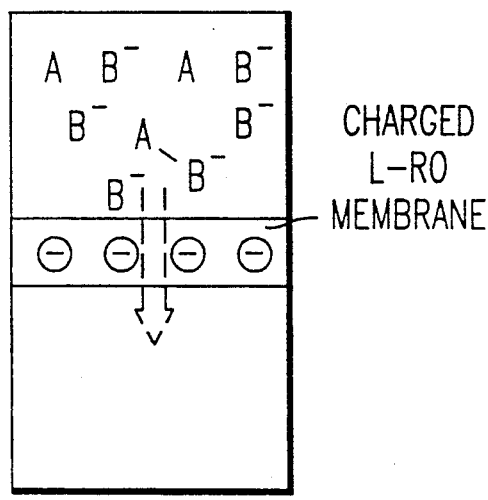
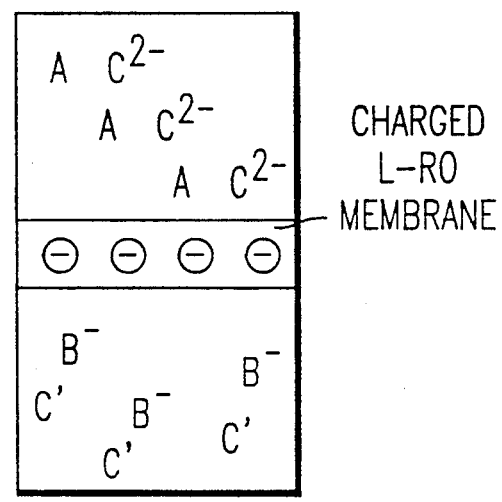
*FIG. 3A*  *FIG. 3B*

5,015,386

METHOD FOR SEPARATION OF ELECTROLYTES, AND METHOD FOR ION EXCHANGE OF ELECTROLYTES WITH COUNTER-IONS

BACKGROUND OF THE INVENTION

1. Field of the Invention

The present invention relates to a method for separating ions with different charges of the same sign in an aqueous solution, using a charged, loose reverse-osmotic membrane (L-RO membrane). It also relates to a method for ion exchange of said substances.

2. Discussion of the Background

In the conventional technique, unnecessary ions in a solution are removed using anion- or cation- exchange resins or by crystallizing the electrolytes into salts with low solubility. With the method using an ion-exchange resin, however, separation of ions whose charge have the same sign is very difficult. Crystallization is effective only when the solubility of the electrolytic salt to be desired is low, and it is inflexible.

With the membrane method, the way in which univalent and bivalent ions in electrodialysis are affected by membrane charge is well known. It is difficult to use electrodialysis in separating univalent and bivalent ions because of the low transfer speed of these electrolytes, and it cannot be used to exchange counter-ions because they migrate in different directions according to their charges.

Separation of electrolytes using a charged ultrafiltration membrane has been studied recently. In this method, pressure is used to push the solution through the membrane, and ions are bound if they have electrolytes from non-electrolytes of identical molecular weight. This permits obtaining the charge needed to bind electrolytes in the membrane using electrolytic solutions of low concentration. This also allows separation of univalent and bivalent ions, since generally the larger the ion charge, the more effectively ions are bound. It is known that a high electrolyte concentration has no effect on the charge of the membrane and lessens the stopping effectiveness despite the ion charge. For this reason, this method of separating using a charged ultrafiltration membrane is not used.

Separation of necessary ingredients from unnecessary ones using a charged membrane is effective when separating ions in a solution which coexist with unnecessary ions of different charges and the same sign, or when the counter-ions of the desired ions coexist with unnecessary ions of different charge and the same sign. Separating electrolytes in low concentration using a charged ultrafiltration membrane is reported to be effective (See the summaries in the Autumn 19th meeting sponsored by the Chemical Engineering Society of Japan, p. 238). Use of an ultrafiltration membrane has no effect on the electric charge of the electrolyte, but shows a drop in its ability to bind electrolytes with increasing electrolytic concentration (summaries in the Autumn 19th meeting sponsored by the Chemical Engineering Society, p. 238). Consequently, an ultrafiltration membrane cannot be employed in treating electrolyte solutions in high concentrations such as fermented liquids and others which need to be separated for industry. This is true when an ion exists alone or when it coexists with other ions despite their charge, and so ions in high concentration cannot be separated by an ultrafiltration membrane.

Therefore, it has been desired to develop a method capable of separating industrially required ions from unnecessary ions even if electrolyte solutions are in relatively high concentration.

SUMMARY OF THE INVENTION

The reason the binding or stopping ability of a charged ultrafiltration membrane decreases with increasing electrolyte concentration is that the charge on the membrane is of low density. It has little effect on the electrolyte due to its large pore size.

But it is known that the water resistance of a membrane generally drops with increasing density of electric charge on the membrane, and consequently the density could not be set more than several meg/ g-polymer. So the present inventors made the pore size of the membrane smaller in order to maintain its stopping power.

The inventors tested using a charged L-RO membrane whose fractional molecular weight was smaller than that of the ultrafiltration membrane from 100 to 1,000 and found out that univalent and bivalent anions (or cations) were separated even in electrolyte solutions of high concentration when certain operating conditions were fulfilled, which lead them to this invention.

The present process for separating electrolytes separates ions with different charges of the same sign, by drawing the anions or cations with the smaller charge through an anion- or cation-charged loose reverse-osmotic membrane in a solution containing ions with at least two or more different ions with charges of the same sign.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

FIG. 2 shows how the charged L-RO membranes may be used for separation of electrolytes.

FIG. 3 shows how the charged L-RO membranes may be used for ion exchange of electrolytes with counterions.

DESCRIPTION OF THE PREFERRED EMBODIMENTS

To exchange electrolytes with counter-ions using the present process, electrolytes whose counter-ions are ion-exchanged are obtained by adding a salt containing counter-ions with a smaller charge, and the same sign, when electrolytes which have a valence which lets them pass through the charged loose reverse-osmotic membrane and have counter ions with a charge of 2 or more are drawn through the membrane.

For example, a sulfonated polysulfone membrane or polyether sulfonic membrane having an anion charged sulfonyl group and also a polysulfone membrane or animated polyether sulfone membrane which are cation-charged may be used as the charged L-RO membrane in this invention.

When these charged L-RO membranes are used, the rejection rate for bivalent ions is higher than that of univalent ones, just as with charged ultrafiltration membranes. When either univalent or bivalent ions exist alone, their rejection rates become lowered with increasing electrolytic concentration. If, as is preferable, both univalent and bivalent ions exist in a ratio where the molarity of univalent ions divided by the molarity of bivalent ions equals 0.5 to 10, the rejection rate of bivalent ions does not fall when the anion or cation concentration is from 5,000 to 200,000 ppm. This enables separation of univalent and bivalent ions.

Either anions or cations will work, and anion- and cation-charged membranes are used depending on the charge of the electrolytes.

The operation pressure of the reverse-osmotic membrane should be 10 kg/f/cm$^2$ or more, preferably 10 to 60 kg.f/cm$^2$, and the flow rate of the feed solution is preferably sufficient to create a turbulent flow. The preferred feed rate is 20 to 200 cm/sec. The preferred temperature range for operation is 5° to 80° C.

Anions which can be separated are, for example, $Cl^-$, $SO_4^{2-}$, $PO_4^{3-}$, or organic acids such as lactic acid, succinic acid, and maleic acid. Cations can be metal ions such as $K^+$, $Na^+$, $Ca^{2+}$, $Mg^{2+}$, $Cu^{2+}$, $Ag^+$, $Fe^{3+}$, $Ni^{2+}$, and $NH_4^+$. In addition, controlling the pH of the solution with acids or alkalies permits various amino acids to be treated as anions or cations. Solutions containing anions with two or more different charges are separated with an anion-charged membrane; solutions with cations use a cation-charged membrane.

The relative concentrations of ions to be separated is determined by the conditions of the charged L-RO membrane and the treatment conditions. Accordingly, it cannot be clearly stated in advance, but the relative concentration ratio (after separation/ before separation), is in the range of about 50 to 100%.

Figure 4:
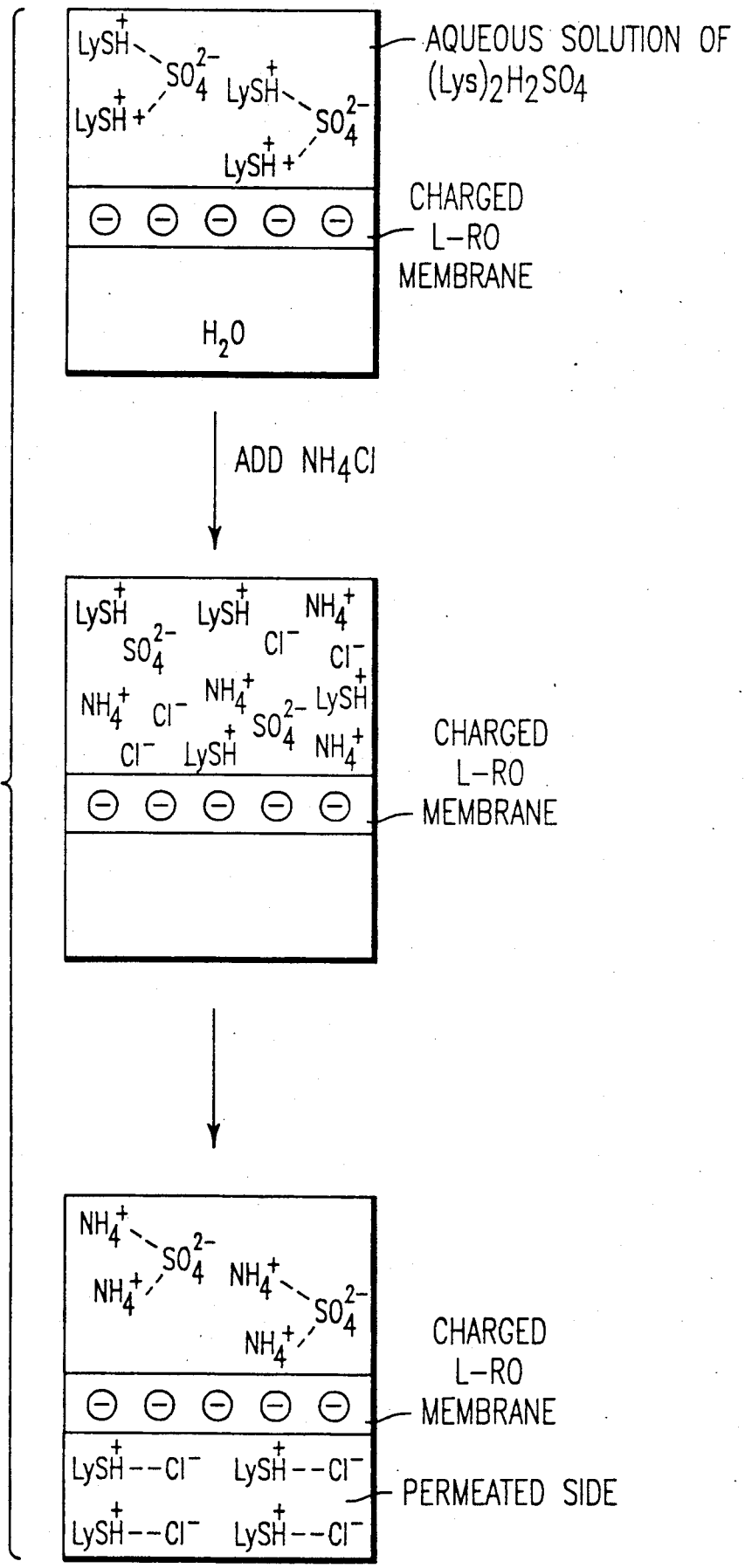
FIG. 4 corresponds to Example 2 of the specification.

Moreover, when the counter-ions of required ingredients are exchanged, ion-separation (e.g. of $(Lys)_2H_2SO_4$) using a charged membrane can be carried out after adding the appropriate salt (e.g. $NH_4Cl$) which contains the ingredient to be exchanged (e.g. $Cl^-$). This allows one to obtain the target ingredients (e.g. LysHCl) whose counter-ions are exchanged with the original, or permeating liquid. FIG. 4 is an illustration of this process.

Impurities in the feed solution are mainly inorganic salts. Other impurities are those materials which are produced by fermentation processes.

When electrolytes to be ion-exchanged have a charge which does not allow them to pass through the charged L-RO membrane and have ions with a charge of three or less, atoms with a charge whose counter-ions are exchanged can be obtained continuously and at high efficiency by adding a salt containing counter-ions with a charge of four or more with the same sign.

Other features of the invention will become apparent in the course of the following descriptions of exemplary embodiments which are given for illustration of the invention and are not intended to be limiting thereof.

EXAMPLES

EXAMPLE 1

Flat anion-charged loose reverse osmotic membranes NTR-7450 (manufactured by Nitto Denko Co., Ltd.) were used for the membranes which have a charged density of 0.8 meq./g-dry membrane and a cutting molecular weight of 20,000. Their effective area is 34 cm$^2$.

The electrolytes to be separated were $Na_2SO_4$ and NaCl. NaCl concentration was adjusted to the range of 1 to 30 g/l after the $SO_4^{2-}/Cl^-$ ratio was controlled to 1.5. The original liquid temperature (25° C.) was maintained during separating. The operating pressure was 20 kg.f/cm$^2$, and the linear velocity of the original liquid at the feed was 43 cm/sec.

Figure 1:
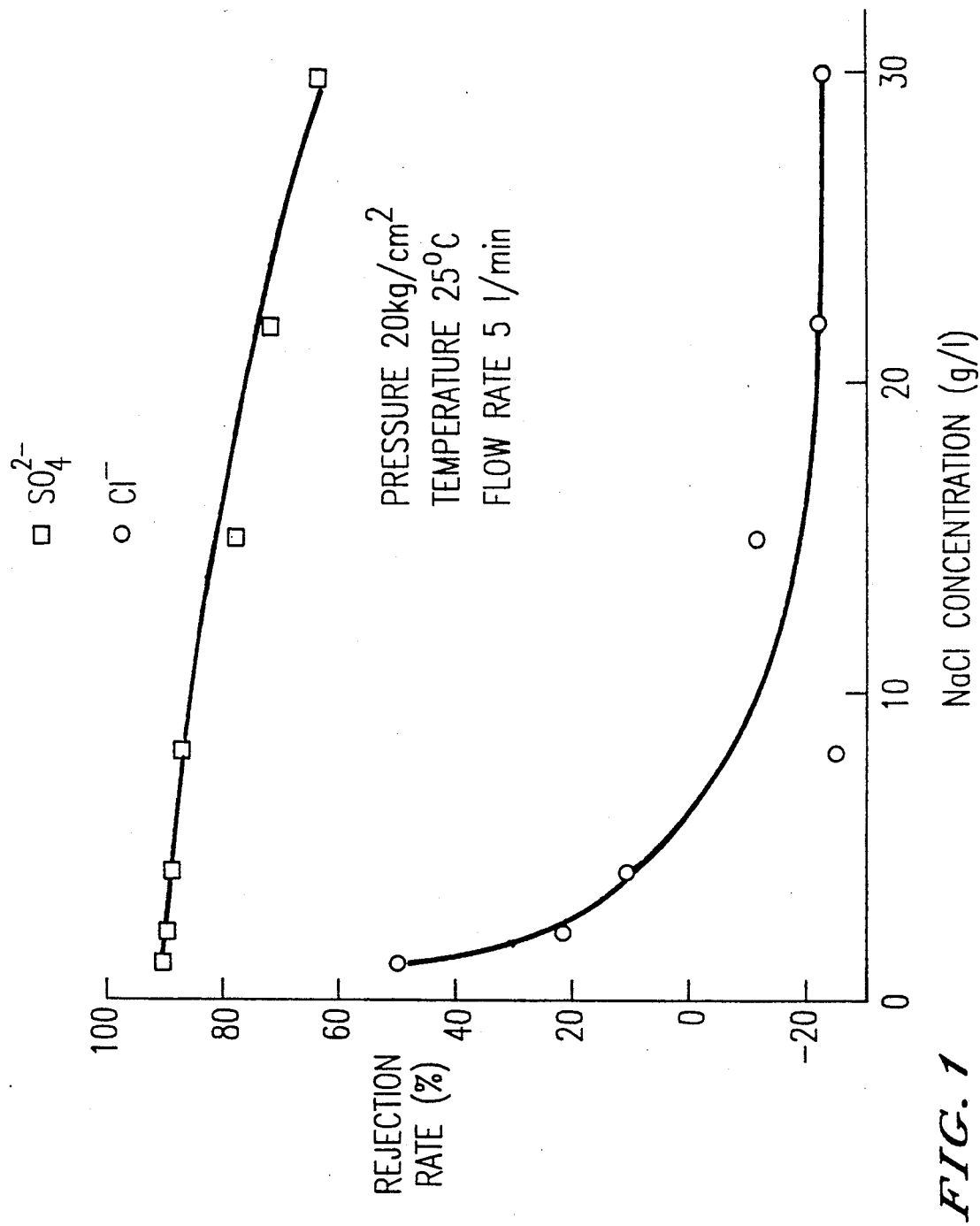
FIG. 1 is a graph showing the relationship between the rejection rate of $SO_4^{2-}/Cl^-$ through an anion L-RO membrane with an NaCl concentration $(SO_4^{2-})Cl^- = 1.5$ constant).

The results are plotted in FIG. 1. The membrane flux was 40 l/m$^2$·hr The rejection rate of $Cl^-$ fell sharply with increasing electrolytic concentration, and was negative when the NaCl concentration was 10 g/l or more. The drop in the rejection rate of $SO_4^{2-}$ was restrained due to an increase in the $Cl^-$ transport volume.

EXAMPLE 2

Experiments in which sulfates composed of counter-ions of lysine are exchanged with chlorine ions were run using the same membrane as Example 1. Membrane separation was conducted by adding ammonium chloride to the lysine sulfate solution. The original liquid concentration of lysine was 5 g/dl and the ammonium chloride added had the same molecular weight as the lysine in the solution.

The results are shown in Table 1. The $Cl^-$ was actively transported in this case too, and a drop in the rejection rate of $SO_4^{2-}$ was restrained. As a result, the counter-ions of lysine in solution were exchanged from $SO_4^{2-}$ to $Cl^-$.

TABLE 1

| Operating pressure [kg/f/cm$^2$] | 20 | 40 |
|---|---|---|
| Apparent rejection rate (%) | | |
| $SO_4^{2-}$ | 76 | 88 |
| $Cl^-$ | −5.5 | 24 |
| Lys$^+$ | 46 | 70 |
| Membrane flux [l/m$^2$·hr] | 42 | 76 |

Since this invention permits separating ions in an electrolyte solution of high concentration, in order of charge and does it efficiently and continuously, it is expected that it will be widely applied to industrial separation and refinement of fermented liquid with various amino acids, and others.

Obviously, numerous modifications variations of the present invention are possible in light of the above teachings. It is therefore to be understood that within the scope of the appended claimed, the invention may be practiced otherwise than as specifically described herein.

What is claimed as new and desired to secured by Letters Patent of the United States is:

1. A method for separating electrolytes which have different charges of the same sign, which comprises causing an electrolyte to pass through a charged loose reverse-osmotic membrane having a charge density of 0.8 meq./g-dry membrane and a cutting molecular weight of 20,000, in an aqueous solution containing at least two electrolytes which have different charges of the same sign, wherein the anion or cation concentration in said solution is in the range of 5,000 to 200,000 ppm, and wherein the charged reverse-osmotic membrane is operated at a pressure of more than 10 kgf/cm$^2$.

2. A method for anion exchange of electrolytes with counter-ions, which comprises adding to a first electrolyte salt a second electrolyte salt containing an anion counter-ion which has a smaller charge than the anion of said first electrolyte salt, and causing the electrolyte salts to pass through a charged loose reverse-osmotic membrane, and whereby counter-ions with a charge of 2 or more are stopped by said membrane, wherein said loose reverse-osmotic membrane has a charge density of 0.8 meq./g-dry membrane and a cutting molecular weight of 20,000.

3. A method for anion exchange of electrolytes with counter-ions, which comprises adding to a first electrolyte salt with an anion counter-ion having a charge of 3 or less a second electrolyte salt containing an anion counter-ion having a charge of 4 or more, and causing the electrolyte salts to pass through a charged loose reverse-osmotic membrane, whereby counter-ions with a charge of 4 or more are stopped by said membrane, wherein said membrane has a charge density of 0.8 meg./g-dry membrane and a cutting molecular weight of 20,000.

* * * * *